United States Patent [19]

Rekoske

[11] Patent Number: 6,096,934
[45] Date of Patent: Aug. 1, 2000

[54] OXIDATIVE COUPLING OF METHANE WITH CARBON CONSERVATION

[75] Inventor: James E. Rekoske, Glenview, Ill.

[73] Assignee: UOP LLC, Des Plaines, Ill.

[21] Appl. No.: 09/208,241

[22] Filed: Dec. 9, 1998

[51] Int. Cl.⁷ .................................. C07C 2/82; C07C 2/84
[52] U.S. Cl. ........................ 585/316; 585/500; 585/823; 585/824; 585/943; 95/139; 95/140; 95/148
[58] Field of Search ...................... 585/316, 500, 585/943, 823, 824; 95/139, 140, 148

[56] References Cited

U.S. PATENT DOCUMENTS

| | | | |
|---|---|---|---|
| 3,890,113 | 6/1975 | Child et al. ........................... | 48/197 R |
| 4,477,267 | 10/1984 | Reiss .......................................... | 55/68 |
| 4,507,517 | 3/1985 | Devries et al. ........................ | 585/415 |
| 4,734,537 | 3/1988 | Devries et al. ........................ | 585/415 |
| 4,849,571 | 7/1989 | Gaffney ................................... | 585/500 |
| 4,937,059 | 6/1990 | Kolts et al. ............................. | 423/230 |
| 5,026,934 | 6/1991 | Bains et al. ............................. | 585/314 |
| 5,118,898 | 6/1992 | Tyler et al. .............................. | 585/500 |
| 5,132,481 | 7/1992 | Do et al. ................................. | 585/500 |
| 5,430,219 | 7/1995 | Sanfilippo et al. ..................... | 585/659 |
| 5,531,808 | 7/1996 | Ojo et al. ................................. | 95/96 |
| 5,750,821 | 5/1998 | Inomata et al. ........................ | 585/943 |

FOREIGN PATENT DOCUMENTS

| | | |
|---|---|---|
| 19530528 | 2/1997 | Germany . |
| 19531453 | 2/1997 | Germany . |

*Primary Examiner*—Walter D. Griffin
*Attorney, Agent, or Firm*—John G. Tolomei; Frank S. Molinaro; Maryann Maas

[57] ABSTRACT

A process for converting methane to ethane and ethylene through oxidative coupling of methane and carbon conservation has been developed. The process begins by contacting methane and an oxygen-containing stream with an oxidative coupling catalyst that is capable of reacting with carbon oxides to form a solid carbonate compound in an oxidative coupling reactor to produce an effluent containing methane, ethane, and ethylene. The solid carbonate compounds are thermally decomposed to the oxidative coupling catalyst by reaction with hot hydrogen. The oxidative coupling catalyst is then available for reuse and a stream containing hydrogen and carbon oxide by-products are produced. The stream containing hydrogen and carbon oxide by-products is contacted with a methanation catalyst in a methanation reactor to produce a stream containing methane and water. The methane is separated, dried, and recycled to the oxidative coupling reactor. Alternatively methane and an oxygen-containing stream may be contacted with an oxidative coupling catalyst in an oxidative coupling reactor to produce an effluent containing methane, ethane, ethylene and carbon oxides. The effluent is passed to an adsorption zone containing an adsorbent capable of selectively adsorbing the carbon oxides. The carbon oxides are desorbed from the adsorbent using hot hydrogen to generate a stream containing hydrogen and carbon oxides which is then contacted with a methanation catalyst in a methanation reactor to produce a stream containing methane and water. The methane is separated, dried, and recycled to the oxidative coupling reactor.

18 Claims, 1 Drawing Sheet

6,096,934

1

OXIDATIVE COUPLING OF METHANE WITH CARBON CONSERVATION

BACKGROUND OF THE INVENTION

Large quantities of methane are available through natural gas and refinery processes such as catalytic cracking, hydrocracking, isomerization, or catalytic reforming. But methane has only minimal value as a chemical or petrochemical feedstock and is therefore often consumed by burning. In comparison, there is significant economic value in ethane and ethylene, which are products of the oxidative coupling of methane. A major drawback to oxidative coupling of methane processes is the low per-pass yield of product, usually less than 30 mole percent, and the high yield of carbon oxide by-products such as carbon monoxide and carbon dioxide. Most attempts to increase product yield have been through new catalyst formulations; see U.S. Pat. No. 4,734,537, U.S. Pat. No. 4,507,517, and Kirk-Othmer *Encyclopedia of Chemical Technology*, 4th ed.; John Wiley & Sons: New York, Vol. 13 pp. 696–697 and 815–816. However, even with new catalysts, the typical yield of ethane and ethylene remains low.

The present invention is accepting of the yield limits with current catalysts and provides a process for the oxidative coupling of methane that compensates for the low product yield of standard catalysts by employing carbon conservation. The carbon oxide by-products of the oxidative coupling reaction are separated from the desired ethane and ethylene products and are reacted to form methane which is recycled to the oxidative coupling of methane reaction zone. There have been other attempts at improving the overall value of oxidative coupling of methane processes in spite of the low yields with several such attempts focusing on making further use of the undesired by-products. For example, U.S. Pat. No. 5,026,934 describes further processing the carbon oxide by-products to form methanol. Other attempts have focused on how to further process the ethane and ethylene produced by the oxidative coupling of methane; see U.S. Pat. No. 5,430,219. At least one reference has disclosed further processing of the ethane and ethylene products along with reacting the carbon monoxide by-product of the oxidative coupling of methane reaction and hydrogen to produce additional $C_2$+hydrocarbons; see U.S. Pat. No. 4,849,571.

The present invention is directed to increasing the ultimate production of ethane and ethylene from the oxidative coupling of methane through carbon conservation and recycle. Undesired carbon oxide by-products from the oxidative coupling reaction are separated from the desired ethane and ethylene products through either chemical reaction with the oxidative coupling catalyst itself or through adsorption. The separated carbon oxide by-products are contacted with a methanation catalyst to form methane which is dried and recycled to the oxidative coupling reactor. Through the carbon conservation and recycle, a greater portion of the available methane is ultimately converted to ethane and ethylene. Thus, the economics of methane oxidative coupling is favorably altered.

SUMMARY OF THE INVENTION

The purpose of the invention is to provide a process for converting methane to ethane and ethylene through oxidative coupling of methane and carbon conservation. One embodiment of the process begins by contacting methane and an oxygen-containing stream with an oxidative coupling catalyst that is capable of reacting with the carbon oxides, carbon monoxide and carbon dioxide, to form solid carbon-

2 ate compounds in an oxidative coupling reactor to produce solid carbonate compounds and an effluent containing methane, ethane, and ethylene. The solid carbonate compounds are thermally decomposed to the oxidative,coupling catalyst by reaction with hot hydrogen. The oxidative coupling catalyst is then available for reuse and a stream containing hydrogen and carbon oxide by-products is produced. The stream containing hydrogen and carbon oxide by-products is contacted with a methanation catalyst in a methanation reactor to produce a stream containing methane and water. Methane is separated from the stream containing methane and water by distillation or adsorption of the water to form dried methane which is recycled to the oxidative coupling reactor.

Another embodiment of the invention begins with contacting methane and an oxygen-containing stream with an oxidative coupling catalyst in an oxidative coupling reactor to produce an effluent containing methane, ethane, ethylene and the carbon oxides, carbon monoxide and carbon dioxide. The effluent is passed to an adsorption zone containing an adsorbent capable of selectively adsorbing the carbon oxides to produce a product stream containing methane, ethane and ethylene. The carbon oxides are desorbed from the adsorbent using hot hydrogen to generate a stream containing hydrogen and carbon oxides. The stream containing hydrogen and carbon oxides is contacted with a methanation catalyst in a methanation reactor to produce a stream containing methane and water. Methane is separated from the stream containing methane and water by distillation or adsorption of the water to form dried methane which is recycled to the oxidative coupling reactor.

BRIEF DESCRIPTION OF THE DRAWINGS

The figures are schematic representations of two embodiments of the present invention.

Figure 1:
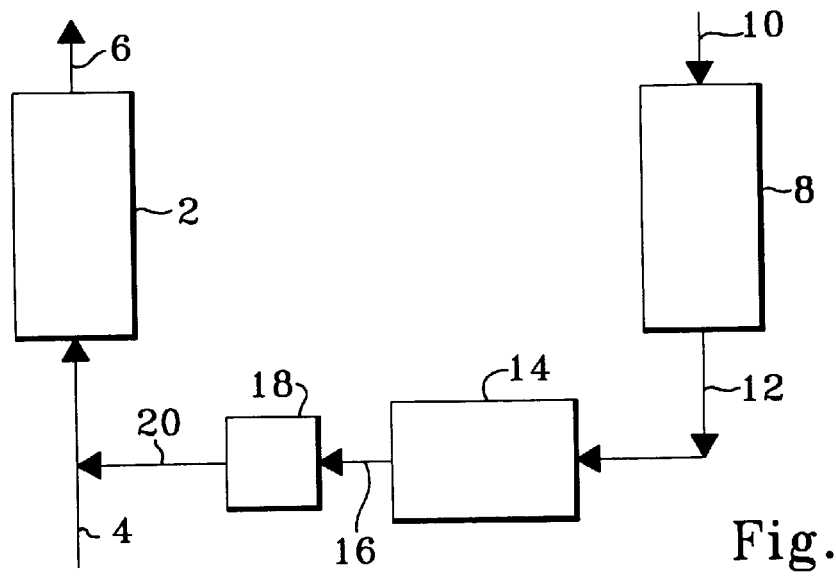
FIG. 1 depicts an embodiment of the invention where the catalyst is chosen with the capability of forming a stable solid carbonate with the carbon oxide by-products of the oxidative coupling reaction and the oxidative coupling reaction zone is operated in the swing bed mode.

The drawings have been simplified by the deletion of a large number of pieces of apparatus customarily employed in processes of this nature which are not specifically required to illustrate the performance of the invention.

DETAILED DESCRIPTION OF THE INVENTION

In general terms, the invention is a process for converting methane to ethane and ethylene by oxidative coupling of methane with the advantage of having carbon oxide by-products separated from the desired products and ultimately recycled in the form of methane. The process of the invention begins with introducing methane and an oxygen-containing stream to an oxidative coupling reactor. The oxygen-containing stream is typically air, but other sources such as purified oxygen are also suitable. The oxidative coupling reactor may be operated in the swing bed, moving bed, or simulated moving bed modes. For ease of understanding, the invention will be described as operating in the preferred swing bed mode with a minimum of two fixed beds; one fixed bed is operated on-line while a second spent bed is regenerated off-line. After the regeneration is complete, the regenerated off-line fixed bed can be "swung" on-line and into service when needed to replace a spent fixed bed. The on-line oxidative coupling reactor is operated at temperatures ranging from about 400° C. to about 1200° C. and preferably from about 700° C. to about 1000° C., pressures ranging from less than 14 psig to about 400 psig, and contains an oxidative coupling catalyst. As the methane and oxygen contact the catalyst, the oxidative coupling of methane reaction is catalyzed and ethane, ethylene, and carbon oxide by-products are produced. The carbon oxide by-products include carbon monoxide and carbon dioxide.

It is preferred that the oxidative coupling catalyst function to both catalyze the oxidative coupling of methane reaction and to concurrently separate carbon oxide by-products from the desired ethane and ethylene products. The preferred catalysts contain an alkali or base metal compound capable of stable carbonate formation under the conditions of the oxidative coupling reactor. As the carbon oxide by-products are formed they react with the catalyst to form a stable solid carbonate and are thereby separated from the vapor phase water, ethane, and ethylene products. For example, if the oxidative coupling catalyst were barium oxide (BaO), some of the BaO would react with byproduct carbon-oxides to form bulk barium carbonate ($BaCO_3$) in solid-mixture with BaO according to the reaction $CO_x + BaO + (2-x)/2\ O_2 \rightarrow BaCO_3$. The carbon oxides would be removed from the vapor phase and immobilized in the carbonate compound thereby leaving only water, methane, ethane, and ethylene in the vapor effluent of the reactor. The alkali or base metal compounds of the catalyst, which are present in either a hydroxide or an oxide form, include lithium, sodium, and other Group IA elements; calcium, barium, and other Group IIA elements; lanthanum, cesium and other lanthanide series elements; as well as bismuth, lead, cadmium, titanium, and nickel which are present either as a metal oxide, hydroxide, or in the metallic form as a promoter. The preferred alkali or base metal compounds are barium, strontium, and lanthanum present in either the hydroxide or oxide form. Examples of specific catalysts include lithium supported on magnesium oxide where the lithium is present in either the hydroxide or oxide form; bismuth supported on calcium oxide where the bismuth is present in either the hydroxide or oxide form; lithium supported on calcium oxide where the lithium is present in either the hydroxide or oxide form; cerium supported on magnesium oxide where the cerium is present in either the hydroxide or oxide form; nickel and lanthanum supported on magnesium oxide where the lanthanum is present in either the hydroxide or oxide form and the nickel is present in the metallic form; and lithium supported on lanthanum oxide where the lithium is present in either the hydroxide or oxide form; or any other metal or metal oxide or hydroxide catalyst which in itself is capable of forming a stable carbonate or any metal or metal oxide or hydroxide catalyst which is promoted with a Group IA, IIA, lanthanide series element present in an oxide or hydroxide form or any additional element capable of forming a stable carbonate. The most preferred catalysts are calcium- and lithium-promoted barium oxide, calcium- and lithium-promoted lanthanum oxide, and calcium- and lithium-promoted magnesium oxide where in each case the calcium and lithium are present in either the hydroxide or oxide form. Catalysts that react with the carbon oxides are known, and such a reaction has been generally regarded as a problem due to the deactivation accompanying the catalyst conversion to a carbonate; see U.S. Pat. No. 5,132,481. The present invention applies what has been previously viewed as a "problem" in an advantageous way to ultimately increase product yield.

In an alternate embodiment of the invention, the oxidative coupling reaction and the separation of carbon oxides take place over two separate zones: a first zone for the oxidative coupling reaction and a second zone for the adsorption and separation of carbon oxide by-products from the effluent of the first zone. In this embodiment the catalyst for the oxidative coupling reaction in the first zone does not form a stable solid carbonate with the carbon oxide by-products, or may form only a negligible amount of stable solid carbonate that is insufficient to satisfactorily separate the carbon oxide by-products from the desired products. Suitable catalysts generally have alkali or alkaline-earth promoters present on alkaline-earth, lanthanide series, or other metal oxides or hydroxides. Specific examples include zirconia-supported ruthenium or nickel where the ruthenium is in the metallic form; crystalline, microporous titanium silicate with a zeolite structure impregnated with ruthenium or rhodium present in the metallic form, as well as sodium supported on magnesium oxide where the sodium is present in the oxide or hydroxide form; tin supported on magnesium oxide where the tin is in the metallic form; lithium supported on lanthanum oxide where the lanthanum is present in the oxide or hydroxide form; manganese supported on zinc oxide where the manganese is present in the oxide or hydroxide form; potassium supported on lanthanum oxide where the potassium is present in the oxide or hydroxide form; and potassium supported on bismuth oxide where the potassium is present in the oxide or hydroxide form; see DE 19531453 and DE 19530528 which are incorporated by reference. See also, Kirk-Othmer *Encyclopedia of Chemical Technology*, 4th ed.; John Wiley & Sons: New York, Vol. 16 pp. 31–32 and 956–957. The most preferred catalysts are sodium, phosphorus, and manganese supported on silica where the sodium phosphorus and manganese are present in the oxide or hydroxide form, sodium, phosphorus, and manganese supported on magnesium oxide where the sodium phosphorus and manganese are present in the oxide or hydroxide form, and lithium supported on sulfated zirconia where the lithium is present in an oxide or hydroxide form. The oxidative coupling reactor is operated at a temperature ranging from about 400° C. to about 1200° C. and a pressure ranging from less than 14 psig to about 400 psig. As the methane and oxygen contact the catalyst, the oxidative coupling of methane is catalyzed and ethane and ethylene are produced. Carbon monoxide and carbon dioxide are produced as undesired by-products. Therefore, the effluent from the oxidative coupling reactor contains methane, ethane, ethylene and carbon oxide by-products.

The effluent is conducted to a second zone containing an adsorbent capable of selectively adsorbing the carbon oxide by-products. Suitable adsorbents include lanthanum oxide with at least one alkali metal hydroxide or oxide, preferably alkali metal hydroxide and more preferably lithium hydroxide as well as alkali and alkaline earth exchanged X- and Y-type zeolites and other suitable zeolitic materials possessing a large adsorption equilibrium constant for carbon oxides. In the second zone, as the effluent contacts the adsorbent, the carbon oxide by-products are selectively adsorbed and separated from the methane, ethane, and ethylene. The second zone, or the adsorption zone, may be operated in a swing bed, moving bed, or simulated moving bed mode at temperatures in the range of about 0° C. to about 400° C. and pressures in the range of from less than 14 psig to about 500 psig.

Whether the oxidative coupling catalyst chemically reacts with the carbon oxide by-products to form a stable solid carbonate, or the effluent of the oxidative coupling reactor is conducted to an adsorption zone containing an adsorbent capable of selectively adsorbing the carbon oxide by products, the carbon oxide by-products are separated from the desired products and are immobilized by a solid phase. The remaining vapor phase components are removed from either the oxidative coupling reactor or the adsorption zone in an effluent stream containing at least methane, ethane, and ethylene. If the oxygen-containing stream that was introduced to the oxidative coupling reactor was air, the effluent stream will also contain oxygen-depleted air. The effluent stream may be distilled to separate the components and methane may be recycled to the oxidative coupling reactor.

When the oxidative coupling catalyst becomes spent through conversion to carbonate compounds or in the embodiment utilizing a reaction zone followed by an adsorption zone when the adsorbent becomes spent, the catalyst or adsorbent may be regenerated. The term "regeneration" as used herein is meant to include both desorption of adsorbed components and reversion of the solid carbonate to the oxidative catalyst and active form of the adsorbent. First, the embodiment where the catalyst has chemically reacted with the carbon oxide by-products will be discussed, and then the sequential zone embodiment will be addressed. In each of the suitable modes of operation for the oxidative coupling reactor there is a point in time when a portion of the catalyst is available for regeneration or reversion. For example, in the swing bed situation when a bed is taken off-line, it may be regenerated. Regeneration of the catalyst is accomplished through reaction with hydrogen that has been heated to a temperature ranging from about 300° C. to about 1000° C. The hot hydrogen acts to thermally decompose the carbonate to its original catalytic form and the carbon oxide by-products. A vapor stream of hydrogen and carbon oxide by-products is generated and removed from the regeneration operation, and reverted catalyst is available for reuse in the oxidative coupling reactor. Similarly, hot hydrogen, or another suitable desorbent, is introduced to spent adsorbent in the adsorption zone of the sequential zone embodiment in order to desorb carbon oxide by-products. The hydrogen is provided at a temperature in the range of from about 300° C. to about 1000° C. The desorbed carbon oxide by-products and hydrogen are removed from the adsorbent in a vapor stream. The regenerated adsorbent is available for reuse.

The carbon oxide by-products and hydrogen generated by either of the embodiments discussed above are conducted to a methanation reactor. The methanation reactor contains a catalyst effective in catalyzing the methanation reaction of carbon monoxide or carbon dioxide and hydrogen to form methane and water. Suitable catalysts are well known in the art and include zirconia-supported ruthenium, rhodium, or nickel where the ruthenium, rhodium, or nickel is present in metallic form; alumina-supported rhodium, nickel, or nickel-tungsten where the rhodium, nickel, or nickel-tungsten are present in the metallic form, and the like; see Conesa, J. C. et al., *J Catal.* 1979, 58, 34; Efstathiou, A. M.; Benneft, C. O. *J. Catal.* 1989, 120, 137; Benedetti, A. et al. *J. Catal.* 1990, 122, 330; Iizuka, T., et al. *J. Catal.* 1982, 76, 1; Ando, H. et al. *J. Alloys and Compounds* 1995, 233, 139; which are all incorporated by reference. The methanation reactor is typically operated in a fixed bed mode but may be operated in a moving bed, swing bed, or simulated moving bed mode. Typical operating conditions of the methanation reactor include pressures ranging from less than 14 psig to about 500 psig and temperatures ranging from about 50° C. to about 500° C. The methane and water produced in the methanation reactor are removed in an effluent which is processed to separate the methane from the water. Suitable separation processes are well known in the art and include such techniques as adsorption and distillation. The preferred technique is adsorption drying using 4A molecular sieve. The dried methane is then recycled to the oxidative coupling reactor thereby conserving carbon. The conservation of carbon is particularly important in reactions such as oxidative coupling because of the low conversion to desired product, and carbon conservation favorably alters the economics of methane oxidative coupling since more of the carbon is ultimately converted to useful products.

Without intending any limitation of the scope of the invention and as merely illustrative, the invention is explained below in specific terms as applied to two particular embodiments of the invention. The first embodiment is one where the catalyst is chosen with the capability of forming a stable solid carbonate with the carbon oxide by-products of the oxidative coupling reaction. The second embodiment described is one where the catalyst does not form a stable solid carbonate with the carbon oxide by-products of the oxidative coupling reaction so the effluent of the oxidative coupling reactor contains carbon oxide by-products. The carbon oxide by-products are adsorbed and separated from the desired products in an adsorption unit.

Turning now to FIG. 1, an oxidative coupling reactor consists of two beds, 2 and 8, operating in a swing bed mode. The catalyst contained in each bed is barium oxide which is effective to catalyze the oxidative coupling reaction and reacts with the carbon oxide by-products to form a stable solid carbonate, barium carbonate. Bed 2 is active, containing largely barium oxide, and is on-line and bed 8 is spent, containing largely barium carbonate, and is off-line. A stream containing methane and air is introduced to bed 2 which is operated at a temperature of about 723° C. and a pressure of about 14 psig. As the methane and oxygen contact the barium oxide catalyst, the oxidative coupling reaction is catalyzed and methane is formed. Carbon oxide by-products are also formed. As the carbon oxide by-products contact the barium oxide, barium carbonate is formed thereby separating the carbon oxide by-products from the desired products. The remaining vapor components, methane, ethane, ethylene, and oxygen-depleted air, are removed from bed 2 via line 6. The components in line 6 may be further separated by distillation to separate the desired ethylene and ethane into a product stream and the unreacted methane into a stream that is recycled to bed 2 (not shown).

Bed 8 is off-line and is spent, i.e., contains largely barium carbonate. Hydrogen is introduced to bed 8 via line 10 at a temperature of 800° C. As the hot hydrogen contacts the barium carbonate, barium oxide and carbon oxides are formed by thermal decomposition. The carbon oxides are carried with the hydrogen flow and removed from bed 8 via line 12. The carbon oxides and hydrogen in line 12 are introduced to methanation reactor 14. Methanation reactor 14 contains zirconia-supported nickel catalyst and is operated at about 290° C. and about 14 psig. As the carbon oxides and hydrogen contact the zirconia-supported nickel catalyst, methane and water are formed. The methane-water mixture is removed from methanation reactor 14 via line 16 and is introduced to drier 18. Drier 18 contains 4A molecular sieve to selectively adsorb the water. Dry methane is removed from drier 18 via line 20 and is combined with the methane feed in line 4 to bed 2. The thermal decomposition, methanation, drying and recycling of methane is continued until as much as possible of the barium carbonate in bed 8 is reverted to the barium oxide catalyst. At that time, bed 8 is considered to be regenerated and ready to be placed on-line. When a significant portion of the barium oxide in bed 2 has been converted to barium carbonate, bed 2 may be swung to the off-line position for regeneration and bed 8 may be placed in service for the oxidative coupling reaction.

Figure 2:
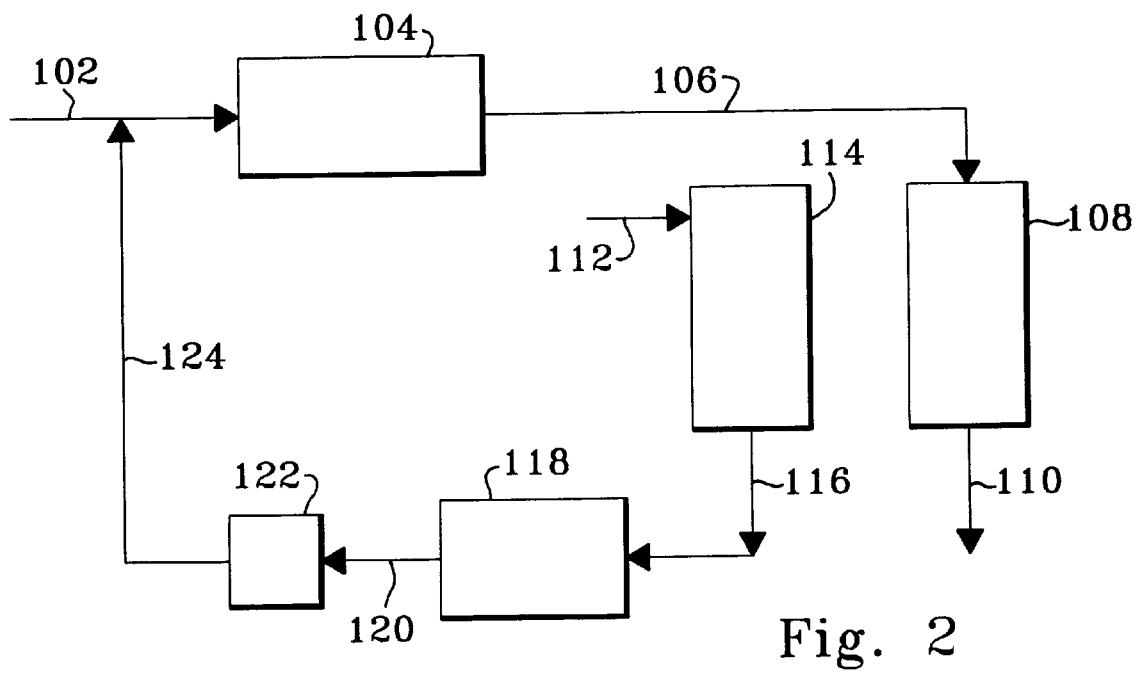
FIG. 2 depicts a second embodiment where the catalyst does not form a stable solid carbonate with the carbon oxide by-products of the oxidative coupling reaction so that the effluent of the oxidative coupling reactor contains carbon oxide by-products. The carbon oxide by-products are adsorbed and separated from the desired products in an adsorption zone operating in a swing bed mode.

Turning now to FIG. 2, the process of the invention requires only a single oxidative coupling reactor 104, with two downstream beds of adsorbent 114 and 108 that are operated in a swing bed mode. The catalyst contained in oxidative coupling reactor 104 is sodium, phosphorus, and manganese supported on silica which is effective to catalyze the oxidative coupling reaction but does not react with the carbon oxide by-products to form a stable solid carbonate in substantial quantities. A stream containing methane and air is introduced to oxidative coupling reactor 104 which is operated at a temperature of about 850° C. and a pressure of about 14 psig. As the methane and oxygen contact the catalyst, the oxidative coupling reaction is catalyzed and methane is formed. Carbon oxide by-products are also formed. The vapor =components, methane, ethane, ethylene, oxygen-depleted air, and carbon oxide by-products are removed from oxidative coupling reactor 104 via line 106. The vapor components are introduced to on-line adsorbent bed 108 that contains sodium-exchanged X-type zeolite which is capable of selectively adsorbing the carbon oxide by-products. With the carbon oxide by-products being adsorbed onto the adsorbent, the remaining vapor components are removed from adsorbent bed 108 via line 110. The components in line 110 may be separated further by distillation to separate the desired ethylene and ethane into a product stream and the unreacted methane into a stream that is recycled to oxidative coupling reactor 104 (not shown).

Adsorbent bed 114 is off-line and is spent, i.e., the adsorbent has no more capacity to adsorb carbon oxide by-products. Hydrogen is introduced to adsorbent bed 114 via line 112 at a temperature of about 600° C. As the hot hydrogen contacts the adsorbent the carbon oxide by-products are desorbed. The carbon oxides are carried with the hydrogen flow and removed from bed 114 via line 116. The carbon oxides and hydrogen in line 116 are introduced to methanation reactor 118. Methanation reactor 118 contains zirconia-supported nickel catalyst and is operated at about 290° C. and about 14 psig. As the carbon oxides and hydrogen contact the zirconia-supported nickel catalyst, methane and water are formed. The methane-water mixture is removed from methanation reactor 118 via line 120 and is introduced to drier 122. Drier 122 contains 4A molecular sieve to selectively adsorb the water. Dry methane is removed from drier 122 via line 124 and is combined with the methane feed in line 102 to oxidative coupling reactor 104.

The desorption of carbon oxide by-products, methanation, drying, and recycling of methane is continued until as much as possible of the carbon oxide by-products in bed 114 have been desorbed. At that time, bed 114 is considered to be regenerated and ready to be placed on-line. When a significant portion of the adsorbent in bed 108 becomes spent, bed 108 may be swung to the off-line position for regeneration and bed 114 may be placed in service for the adsorption of carbon oxide by-products.

It must be emphasized that the above description is merely illustrative of a preferred embodiment and is not intended as an undue limitation on the generally broad scope of the invention. Moreover, while the description is narrow in scope, one skilled in the art would understand how to extrapolate to the broader scope of the invention. For example, operating at different conditions and using different catalysts and adsorbents can be readily extrapolated from the foregoing description.

What is claimed is:

1. A process for converting methane to ethane and ethylene comprising:
    a) contacting, in an oxidative coupling reactor under oxidative coupling conditions, methane and an oxygen-containing stream with an oxidative coupling catalyst that is capable of reacting with carbon monoxide and carbon dioxide to form a solid carbonate compound to produce solid carbonate compounds and a gas stream containing at least methane, ethane, and ethylene;
    b) thermally decomposing the solid carbonate compounds to the oxidative coupling catalyst by reacting with hydrogen at a temperature ranging from about 300° C. to about 1000° C. to regenerate the oxidative coupling catalyst and afford a gas stream containing hydrogen and carbon oxides;
    c) contacting, in a methanation reactor under methanation conditions, the stream containing hydrogen and carbon oxides with a methanation catalyst to produce a stream containing methane and water;
    d) separating methane from the stream containing methane and water to form a stream containing dried methane; and
    e) recycling the stream containing dried methane to the oxidative coupling reactor.

2. The process of claim 1 wherein the oxidative coupling catalyst is selected from the group consisting of calcium- and lithium-promoted barium oxide, calcium- and lithium-promoted lanthanum oxide, and calcium- and lithium-promoted magnesium oxide.

3. The process of claim 1 wherein the methanation catalyst is selected from the group consisting of zirconium-supported ruthenium, rhodium, or nickel, and alumina-supported rhodium, nickel, or nickel-tungsten.

4. The process of claim 1 wherein the oxidative coupling reactor is operated in a mode selected from the group consisting of swing bed, moving bed, and simulated moving bed.

5. The process of claim 1 wherein the oxidative coupling conditions are a temperature in the range of about 400° C. to about 1200° C. and a pressure in the range of about 14 psig to about 400 psig.

6. The process of claim 1 further comprising separating the stream containing at least methane, ethane, and ethylene into a stream containing methane and a stream containing ethane and ethylene and recycling the stream containing methane to the oxidative coupling reactor.

7. The process of claim 1 wherein the methanation reactor is operated in a mode selected form the group consisting of fixed bed, swing bed, moving bed, and simulated moving bed.

8. The process of claim 1 wherein the methanation reactor is operated at a temperature in the range of about 50° C. to about 500° C. and a pressure in the range of about 14 psig to about 500 psig.

9. A process for converting methane to ethane and ethylene comprising:
    a) contacting, under oxidative coupling conditions, methane and an oxygen-containing stream with an oxidative coupling catalyst in an oxidative coupling reactor to produce an effluent containing at least methane, ethane, ethylene, and the carbon oxides, carbon monoxide and carbon dioxide;

b) passing the effluent to an adsorption unit containing an adsorbent capable of selectively adsorbing the carbon oxides to produce a stream containing at least methane, ethane and ethylene;

c) desorbing the carbon oxides from the adsorbent using hydrogen to generate a stream containing hydrogen and carbon oxides;

d) contacting, in a methanation reactor at methanation conditions, the stream containing hydrogen and carbon oxides with a methanation catalyst to produce a stream containing methane and water;

e) separating methane from the stream containing methane and water to form a stream containing dried methane; and f) recycling the stream containing dried methane to the oxidative coupling reactor.

10. The process of claim 9 wherein the hydrogen for desorption is at a temperature ranging from about 300° C. to about 1000° C.

11. The process of claim 9 wherein the oxidative coupling catalyst is selected from the group consisting of calcium- and lithium-promoted barium oxide, calcium- and lithium-promoted lanthanum oxide, and calcium- and lithium-promoted magnesium oxide.

12. The process of claim 9 wherein the adsorbent is selected from the group consisting of (a) a mixture of lanthanum oxide and at least one alkali metal hydroxide or oxide and (b) alkali and alkaline earth exchanged zeolite X and zeolite Y.

13. The process of claim 9 wherein the methanation catalyst is selected from the group consisting of zirconium-supported ruthenium, rhodium, or nickel, and alumina-supported rhodium, nickel, or nickel-tungsten.

14. The process of claim 9 wherein the oxidative coupling reactor is operated in a mode selected from the group consisting of a swing bed, a moving bed, and a simulated moving bed.

15. The process of claim 9 wherein the oxidative coupling conditions are a temperature in the range of about 400° C. to about 1200° C. and a pressure in the range of about 14 psig to about 400 psig.

16. The process of claim 9 further comprising separating the stream containing at least methane, ethane, and ethylene into a stream containing methane and a stream containing ethane and ethylene, and recycling the stream containing methane to the oxidative coupling reactor.

17. The process of claim 9 wherein the methanation reactor is operated in a mode selected form the group consisting of fixed bed, swing bed, moving bed, and simulated moving bed.

18. The process of claim 9 wherein the methanation conditions are a temperature in the range of about 50° C. to about 500° C. and a pressure in the range of about 14 psig to about 500 psig.

* * * * *